United States Patent
Jach et al.

(10) Patent No.: US 6,375,816 B1
(45) Date of Patent: Apr. 23, 2002

(54) SENSOR ELEMENT FOR LIMITING-CURRENT SENSORS FOR DETERMINING THE LAMBDA VALUE OF GAS MIXTURES

(75) Inventors: Olaf Jach, Boeblingen (DE); Harald Neumann, Farmington Hills, MI (US); Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/460,462

(22) Filed: Dec. 14, 1999

(30) Foreign Application Priority Data

Dec. 14, 1998 (DE) .......................................... 198 57 471

(51) Int. Cl.$^7$ ............................................ G01N 27/407
(52) U.S. Cl. ..................................... 204/425; 204/426
(58) Field of Search .................................. 204/421–429

(56) References Cited

U.S. PATENT DOCUMENTS 5,098,549 A * 3/1992 Friese et al.
5,314,604 A * 5/1994 Friese et al.
5,507,937 A * 4/1996 Renz et al.

FOREIGN PATENT DOCUMENTS

DE 35 43 759 7/1986

* cited by examiner

*Primary Examiner*—T. Tung
(74) *Attorney, Agent, or Firm*—Kenyon & Kenyon

(57) ABSTRACT

A sensor element for limiting-current sensors for determining the lambda value of gas mixtures, in particular of exhaust gases from internal combustion engines. The sensor element has inner and outer pump electrodes arranged on a solid electrolyte foil. The inner pump electrode is arranged in a diffusion channel that is bordered by a diffusion barrier, the pump electrode lying in the diffusion direction of the gas mixture downstream of the diffusion barrier. The gas entry hole, essentially perpendicular to the surface of the solid electrolyte foil, is led through the solid electrolyte foil into the diffusion channel. The diffusion barrier is arranged so as to be set back in the diffusion channel from the interior wall of the gas entry hole. For manufacturing the sensor element, a chamber created upstream of the diffusion barrier is filled with a cavity-creating material, which evaporates in the sintering of the sensor element and thus forms a cavity in the diffusion channel.

9 Claims, 1 Drawing Sheet

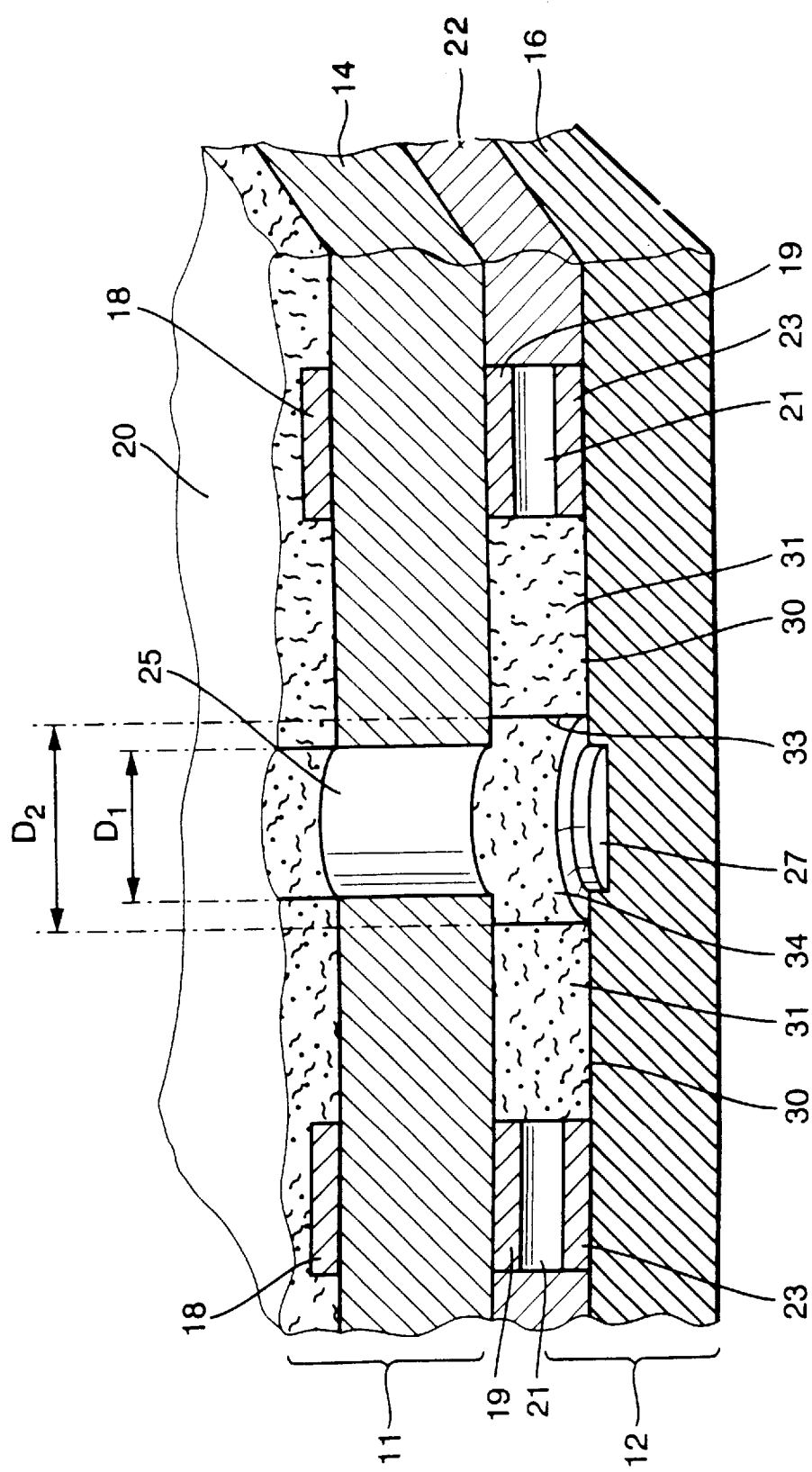

SENSOR ELEMENT FOR LIMITING-CURRENT SENSORS FOR DETERMINING THE LAMBDA VALUE OF GAS MIXTURES

BACKGROUND INFORMATION

In sensor elements that operate according to the limiting current principle, the limiting diffusion current is measured at a constant voltage applied to the two electrodes of the sensor element. This limiting diffusion current in an exhaust gas arising through combustion processes is dependent on the oxygen concentration as long as the diffusion of the gas at the so-called pump electrode determines the speed of the ongoing reaction. On the basis of a simplified and cost-effective production method, in recent years the manufacture of sensor elements using ceramic-foil and silk-screen technology has proven in practice to be advantageous. In a simple and efficient manner, planar sensor elements, based on wafer or foil-shaped oxygen-ion-conductive solid electrolytes, composed, e.g., of stabilized zirconium dioxide, can be manufactured that are coated on both sides having an inner and an outer pump electrode, respectively, and having the associated printed circuit trace. The inner pump electrode, in this context, is located in the edge area of the diffusion channel through which the measuring gas is fed. In the diffusion channel, a diffusion barrier, filled with a porous material, is formed constituting the gas diffusion resistance.

German Patent No. 35 43 759 describes a sensor element that includes a pump cell and a sensor cell, which are arranged in coating layers that are on top of each other. The sensor elements of this type are also designated as broad-band (wideband) sensors, since they can detect the oxygen concentration of fuel/air mixtures ranging from lean to rich. The inner pump electrode of the pump cell and the measuring electrode of the sensor cell, in this context, are arranged opposite each other in a common measuring gas chamber, which at the same time forms the diffusion channel. The diffusion barrier is located in the diffusion channel upstream of the inner pump electrode and the measuring electrode in the direction of diffusion. A gas entry hole is led through the solid electrolyte foils on top thereof and through the layer thickness of the diffusion barrier, so that the inner cylinder wall of the diffusion barrier is part of the gas entry hole.

The manufacture of the diffusion barrier in the aforementioned sensor elements takes place such that a circular silk-screen layer is applied onto the corresponding solid electrolyte foil upstream of the electrodes using a silk-screen paste made, e.g., of $ZrO_2$ and mixed with a pore-forming material. In the center of this silk-screen layer, once all the solid electrolyte foils have been laminated together, the gas entry hole is bored, penetrating at least the entire diffusion barrier. Upon sintering the solid electrolyte foils that have been laminated together, the porous diffusion barrier is then formed along with the hollow measuring gas chamber positioned upstream of the diffusion barrier.

In generating the gas entry hole, in the event of faulty boring parameters (speed, wear in the boring tool), it comes about that the material of the solid electrolyte foil plugs the pores in the inner cylinder wall of the diffusion barrier. This leads to a reduction of the gas entry cross-section after sintering, which ultimately means a large dispersion of the diffusion resistance. In addition, the disadvantage arises that the bored gas entry hole can deviate from the midpoint of the circular silk-screen layer of the diffusion barrier. This deviation leads to a shortening of the diffusion distance of the diffusion barrier and thus to a further alteration of the diffusion resistance. Furthermore, contamination, building up as a rule on the entry surface of the diffusion barrier, leads to a change in the sensor characteristic curve.

SUMMARY OF THE INVENTION

The sensor element of the present invention has the advantage that, when the gas entry hole is bored, the material of the solid electrolyte foils cannot clog the pores of the inner cylinder wall of the diffusion barrier. As a result, the diffusion resistance of the diffusion barrier is not impaired. In addition, a deviation of the centering of the gas entry hole only exerts an influence on the diffusion resistance of the diffusion barrier if the centering exceeds the difference between the boring radius and the inner radius of the diffusion barrier. Furthermore, as a result of the set-back inner wall of the diffusion barrier, the latter is shielded against contamination during extended engine use.

The method of the present invention has the advantage that as a result of the cavity-creating material, it is possible to produce a more defined inner diameter of the diffusion barrier, the cavity-creating material evaporating during the sintering of the sensor element and creating an inner chamber upstream of the diffusion hole.

It has proved to be advantageous to dispose the diffusion barrier so as to be set back roughly 0.1 to 0.3 mm from the wall of the gas entry hole. An advantageous refinement of the method involves pressing the inner chamber upstream of the diffusion barrier together with the cavity of the measuring gas chamber. Due to the shorter diffusion distance, a more planar diffusion barrier can also be used, that can be pressed in fewer silk-screen steps so as not to form cracks.

BRIEF DESCRIPTION OF THE DRAWINGS

The FIGURE depicts one part of the sensor element in cross section.

DETAILED DESCRIPTION

The FIGURE depicts a schematic, enlarged representation of a cross-section of a sensor element, which can be manufactured using ceramic-foil and silk-screen technology. The sensor element depicted in the FIGURE is a so-called broadband sensor, which has a pump cell 11, operating in accordance with the limiting-current principle, and a measuring cell 12 (Nernst cell). In addition, the sensor element has an integrated resistance heater, which is not depicted. However, this design does not represent a limitation of the present invention to this specific embodiment. The present invention is equally applicable to pump cells that operate without the cooperation of a measuring cell.

The sensor element depicted in the FIGURE only in a cutaway view is essentially composed of four solid electrolyte foils laminated together, of which only a first solid electrolyte foil 14 and a second solid electrolyte foil 16 are depicted. On solid electrolyte foil 14 is located an outer pump electrode 18 and an inner pump electrode 19. Above outer pump electrode 18 is located a porous protective layer 20. Inner pump electrode 19 is configured so as to be annular and is located in a measuring gas chamber 21, in which, opposite inner pump electrode 19, a measuring electrode 23 is located on second solid electrolyte foil 16. Outer pump electrode 18 and inner pump electrode 19 together form pump cell 11. Measuring electrode 23 cooperates with a reference electrode (not shown), which is arranged in a reference channel (not shown) and, for example, is in contact with the air as the reference atmosphere.

Between inner pump electrode 19 and measuring electrode 23, a diffusion channel 30 extends in the coating layer 22 between solid electrolyte foils 14, 16. Upstream of electrodes 19, 23, a porous diffusion barrier 31 is located in diffusion channel 30.

In addition, sensor element has a gas entry hole 25, which leads to diffusion channel 30 and, for example, extends as a blind hole through first solid electrolyte foil 14 and diffusion channel 30 into second solid electrolyte foil 16. As a result, gas entry hole 25 in second solid electrolyte foil 16 forms a dead volume 27, in which particles carried in the gas mixture can be deposited. Diffusion barrier 31 is configured in an annular fashion around gas entry hole 25.

Gas entry hole 25 has a diameter D1 of, for example, 0.4 mm. Annular diffusion barrier 31 having inner cylinder wall 33 borders a cylindrical interior chamber 34, which has an interior diameter D2 of, for example, 0.6 mm. Thus cylinder wall 33 of diffusion barrier 31 is set back by 0.1 mm from the interior wall of gas entry hole 25. The radial distance from the interior wall of gas entry hole 25 to cylinder wall 33 of diffusion barrier 31 can be from 0.10 to 0.30 mm. This radial distance is set by the ratio of diameters D1 and D2.

For manufacturing the sensor element of the present invention, ceramic foils are used made of oxygen-ion-conductive solid electrolytes, such as zirconium dioxide stabilized using $Y_2O_3$. The foils, in this context, have a thickness of from 0.25 to 0.30 mm. The foils are imprinted with the electrodes and the associated printed circuit traces, for example, using silk-screen technology. The electrodes and the printed circuit traces are composed, for example, of platinum cermet. The electrodes have a thickness of, for example, 18 to 15 $\mu$m. In addition to electrodes 18, 19, and 23 and the undepicted layers, diffusion barrier 31 is impressed onto second solid electrolyte foil 16 as a ring having an external diameter of, for example, 2 mm and an internal diameter D2 of, for example, 0.6 mm. For configuring interior chamber 34, a cavity paste is pressed into the circular interior surface of diffusion barrier 31. Simultaneously with the pressing of the interior surface of diffusion barrier 31, the surface of the later cavity of measuring gas chamber 21 is also pressed using a cavity paste. The cavity pastes for interior chamber 34 and the cavity of measuring gas chamber 21 are composed, for example, of theobromine, which in the later sintering process burns off and evaporates, respectively, and, in the process, forms the cavities between solid electrolyte foils 14,16 for interior chamber 34 and measuring gas chamber 21.

For generating the pores in diffusion barrier 31, cavity-creating materials are also inserted into the ceramic material, and also burn off during sintering, in the process, generating the open porosity. On the basis of the porosity of diffusion barrier 31, the diffusion resistance, inter alia, is set. By way of example, the material of these solid electrolyte foils is suitable as material for diffusion barrier 31. However, it is equally possible instead of a $ZrO_2$ material to use $Al_2O_3$ for diffusion barrier 31.

The finished, pressed solid electrolyte foils are laminated together. After the lamination, gas entry hole 25 is introduced through first solid electrolyte foil 14, for example, using conventional, metal-cutting bore-hole technology. In this context, the bore hole continues, through the cavity-creating material in interior chamber 34, into the bordering second electrolyte foil 16. Since cylinder wall 33 of diffusion barrier 31 is set back from bore hole diameter D1, the drill used for introducing gas entry hole 25 does not come into contact with diffusion barrier 31. In this way, it is avoided that the material of solid electrolyte foil 14 clogs or obstructs the pores on cylinder wall 33 of diffusion barrier 31.

At the same time, the distance between the interior wall of gas entry hole 25 and cylinder wall 33 of diffusion barrier 31 assures that a centering tolerance is created for the introduction of diffusion hole 25, the tolerance amounting to 0.1 mm radially given a diameter D1 of 0.4 mm and an inner diameter D2 of 0.6 mm. A sintering tolerance of 0.125 mm results at D1 of 0.4 mm and at D2 of 0.65 mm.

What is claimed is:

1. A sensor element for determining a lambda value of an exhaust gas from an internal combustion engine, comprising:
   a solid electrolyte foil having a surface;
   an inner pump electrode situated on the solid electrolyte foil;
   an outer pump electrode situated on the solid electrolyte foil; and
   a diffusion barrier bordering a diffusion channel, the inner pump electrode being situated in the diffusion channel, a gas entry hole being substantially perpendicular to the surface of the solid electrolyte foil and leading through the solid electrolyte foil into the diffusion channel, the diffusion barrier being set back in the diffusion channel from an inner wall of the gas entry hole.

2. The sensor element according to claim 1, further comprising a chamber situated upstream of the diffusion barrier in a diffusion direction of the exhaust gas in the diffusion channel, the gas entry hole leading to the chamber.

3. The sensor element according to claim 1, wherein the diffusion barrier is set back by about 0.1 to 0.3 mm from the inner wall of the gas entry hole.

4. The sensor element according to claim 1, wherein the diffusion barrier is configured in an annular fashion around the gas entry hole.

5. The sensor element according to claim 4, wherein the diffusion barrier has an interior diameter of about 0.5 to 0.8 mm and the gas entry hole has a diameter of about 0.3 to 0.5 mm.

6. The sensor element according to claim 4, wherein the annular diffusion barrier has an outer diameter of about 2 mm.

7. The sensor element according to claim 1, wherein the diffusion barrier is arranged upstream of the inner pump electrode in a diffusion direction of the exhaust gas such that a cavity is formed as a measuring gas chamber in the diffusion channel.

8. The sensor element according to claim 1, wherein:
   a chamber situated upstream of the diffusion barrier is formed by a cavity-creating material evaporating during sintering of the sensor element.

9. The sensor element according to claim 8, wherein:
   a gas measuring chamber is formed by a further cavity-creating material evaporating during sintering of the sensor element.

* * * * *